US012575970B2

(12) United States Patent
Micheletti

(10) Patent No.: US 12,575,970 B2
(45) Date of Patent: Mar. 17, 2026

(54) MULTIFUNCTION OPHTHALMIC BLADE

(71) Applicant: Ophthalmic Neo-Innovations of Texas, LLC, Sugar Land, TX (US)

(72) Inventor: John Morgan Micheletti, Sugar Land, TX (US)

( * ) Notice: Subject to any disclaimer, the term of this patent is extended or adjusted under 35 U.S.C. 154(b) by 260 days.

(21) Appl. No.: 18/486,154

(22) Filed: Oct. 12, 2023

(65) Prior Publication Data

US 2024/0122752 A1 Apr. 18, 2024

Related U.S. Application Data

(60) Provisional application No. 63/415,657, filed on Oct. 13, 2022.

(51) Int. Cl.
*A61F 9/007* (2006.01)
*A61B 17/3211* (2006.01)

(52) U.S. Cl.
CPC . *A61F 9/00754* (2013.01); *A61B 2017/32113* (2013.01)

(58) Field of Classification Search
CPC .... A61F 9/0133–0136; A61F 9/00736–00754; A61B 2017/32113; A61B 17/3211
See application file for complete search history.

(56) References Cited

U.S. PATENT DOCUMENTS

| | | | |
|---|---|---|---|
| D294,861 S | 3/1988 | Detsch | |
| 5,217,477 A | 6/1993 | Lager | |
| 5,224,950 A * | 7/1993 | Prywes | A61F 9/0133 |
| | | | 606/166 |
| 5,437,657 A | 8/1995 | Epstein | |
| 6,125,294 A | 9/2000 | Scholl et al. | |
| 6,497,712 B1 | 12/2002 | Feaster | |
| 6,599,305 B1 | 7/2003 | Feingold | |
| 7,041,114 B2 | 5/2006 | Dan | |
| 7,374,566 B1 | 5/2008 | Schossau | |
| 8,875,405 B2 | 11/2014 | Trees et al. | |
| 11,134,979 B2 | 10/2021 | Morawski et al. | |
| 2002/0161365 A1 | 10/2002 | Martins | |
| 2003/0088258 A1 * | 5/2003 | Feaster | A61F 9/0133 |
| | | | 606/166 |
| 2008/0215078 A1 * | 9/2008 | Bennett | A61F 9/00736 |
| | | | 606/166 |
| 2012/0035636 A1 | 2/2012 | Daxer | |
| 2018/0133056 A1 * | 5/2018 | Kahook | A61F 9/00736 |
| 2022/0023100 A1 * | 1/2022 | Chan | A61F 9/0133 |
| 2022/0265471 A1 * | 8/2022 | Kuo | A61F 9/00736 |
| 2023/0000682 A1 | 1/2023 | Nallakrishnan et al. | |

FOREIGN PATENT DOCUMENTS

WO 2004112665 A1 12/2004

* cited by examiner

*Primary Examiner* — Brigid K Byrd
(74) *Attorney, Agent, or Firm* — Henry L. Ehrlich

(57) ABSTRACT

An ophthalmic instrument includes a blade laterally symmetric about a longitudinal axis with a first triangular portion having first opposed cutting edges and a first longitudinal length extending from an anterior tip to a first position, the first position having a first width, a second portion having parallel second edges and a second longitudinal length extending from the first position to a second position, and a third portion having third opposed cutting edges and a third longitudinal length extending from the second position to a third position, the third position having a third width that is greater than the first width.

22 Claims, 6 Drawing Sheets

MULTIFUNCTION OPHTHALMIC BLADE

TECHNICAL FIELD

This disclosure relates in general to the field of surgical instruments for ophthalmological procedures for treatment of eye diseases, such as cataract, and more particular to a blade for incorporating for making corneal incisions.

BACKGROUND

This section provides background information to facilitate a better understanding of the various aspects of the disclosure and is not an admission of prior art.

Cataract surgery is the most commonly performed surgery in the United States and results with removal of a cataract and implantation of an intraocular lens (IOL). Nearly 3-4 milling people a year have cataract surgery and the number continues to increase. There is a significant amount of waste generated from cataract surgery due to the multiple single-use instruments required for each procedure.

SUMMARY

An exemplary ophthalmic instrument includes a blade extending in a horizontal plane along a longitudinal axis and a lateral axis orthogonal to the longitudinal axis, the blade is laterally symmetric about the longitudinal axis and includes a first triangular portion having first opposed cutting edges and a first longitudinal length extending from an anterior tip to a first position, the first position having a first width parallel to the lateral axis, a second portion having parallel second edges and a second longitudinal length extending from the first position to a second position, and a third portion having third opposed cutting edges and a third longitudinal length extending from the second position to a third position, the third position having a third width that is greater than the first width.

Another exemplary ophthalmic instrument includes a blade extending in a horizontal plane along a central longitudinal axis and a lateral axis orthogonal to the longitudinal axis, the blade laterally symmetric about the central longitudinal axis, where the blade includes a first triangular portion, bisected by central longitudinal axis, having first opposed cutting edges, and a first longitudinal length extending from an anterior tip to a first position, the first position having a first width parallel to the lateral axis, a second portion having parallel second edges and a second longitudinal length extending from the first position to a second position, and a third portion having third opposed cutting edges and a third longitudinal length extending from the second position to a third position, the third position having a third width that is greater than the first width. The first triangular portion and the second portion are on an anterior piece of material and the third opposed cutting edges are on one or more lateral pieces of material different from the anterior piece of material.

The ophthalmic instrument may further include a handle attached to the blade and a guard attached to the handle in a partial operational position where the third portion is inside the guard, and the first triangular portion and the second portion are outside of the guard. In the partial operational position, the blade can be used to create an incision in a cornea with the first triangular portion without exposing the third portion to cutting the cornea. The guard is moveable to a full operational position to expose all of the cutting edges of the blade.

Another exemplary ophthalmic instrument a handle and a blade extending in a horizontal plane along a longitudinal axis and a lateral axis orthogonal to the longitudinal axis, the blade laterally symmetric about the longitudinal axis, where the blade includes a first triangular portion having first opposed cutting edges and a first longitudinal length extending from an anterior tip to a first position, the first position having a first width along the lateral axis of about 1 mm, a second portion having parallel second edges and a second longitudinal length extending from the first position to a second position, the second longitudinal length about 2 mm or greater, a third portion having third opposed cutting edges and a third longitudinal length extending from the second position to a third position, the third position having a third width of about 2.0 to 3.4 mm, and a terminal portion extending longitudinally from the third position to an elbow extending to the handle at an elbow angle less than 180 degrees to the horizontal plane, and the terminal portion having a terminal width narrowing from the third position.

The ophthalmic instrument may further include a guard having a first leg generally orthogonal to a second leg, wherein in use and in a partial operational position the first leg is attached to the handle, the third portion is inside of the second leg, and the first triangular portion and the second portion are positioned outside of the guard. The guard can be moved to a full operational position exposing all of the cutting edges of the blade.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion. As will be understood by those skilled in the art with the benefit of this disclosure, elements and arrangements of the various figures can be used together and in configurations not specifically illustrated without departing from the scope of this disclosure.

DETAILED DESCRIPTION

Figure 1:
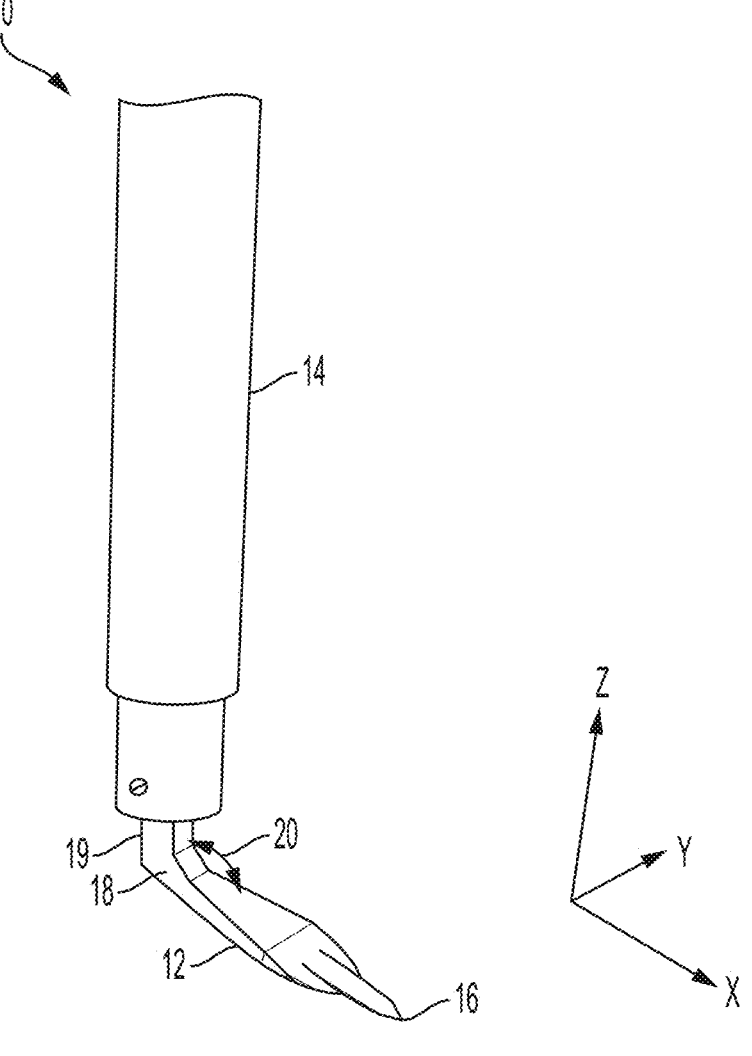
FIG. 1 illustrates an exemplary ophthalmic instrument with a multifunction ophthalmic blade according to one or more aspects of the disclosure.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

Cataract surgery requires multiple incisions in the cornea, most commonly consisting of a smaller "side port" incision of approximately 1 mm and a main "wound" consisting of a 1.4 mm to 3.2 mm incision. Additionally, an instrument called a cystotome is used to enter the anterior capsule. Each of these incisions are performed with a different single use instrument. There currently exists no option for a single instrument to create both corneal incisions of varying sizes and the initial incision into the anterior capsule. Embodiments of the ophthalmic blade address all three of these functions in a single device, which improves surgical efficiency and reduces waste.

Figure 2:
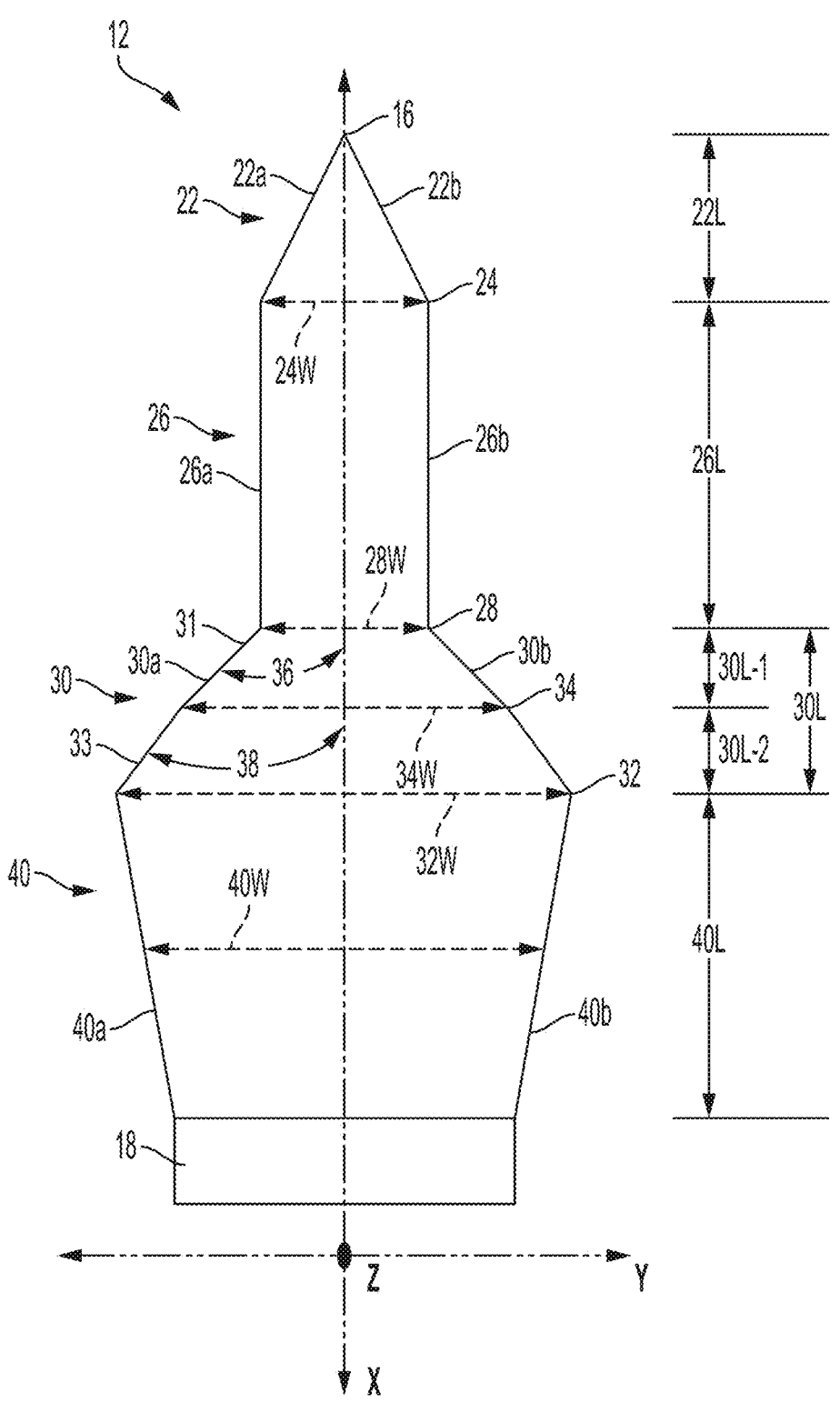
FIG. 2 illustrates an exemplary ophthalmic instrument in the form of a multifunction ophthalmic blade according to one or more aspects of the disclosure.

FIGS. 1 and 2 depict three mutually orthogonal directions X, Y, and Z forming a three-dimensional frame of reference XYZ. Longitudinal axis X corresponds to the axis that extends through the center of the blade in the fore and aft directions. Transverse or lateral axis Y is perpendicular to longitudinal axis X and corresponds to the width of the blade. The X-Y plane is considered to be a horizontal plane. Vertical axis Z is oriented perpendicular with respect to the X-Y plane.

FIG. 1 illustrates an exemplary embodiment of an ophthalmic instrument, e.g., a surgical knife, generally denoted by the numeral 10. Instrument 10 includes a blade 12 that in use is attached to a handle 14. Blade 12 is a generally extends in a horizontal plane (X-Y plane) from an anterior tip 16 to an aft elbow 18. In this example elbow 18 includes an arm 19 that extends to handle 14 at an elbow angle 20 of about 90 degrees to the horizontal plane. Blade 12 may be removably attached via various mechanism so that the blade can be removed, and the handle can be reused. In some embodiments, elbow angle 20 may be 180 degrees, such that the handle is parallel with blade. Elbow angle 20 is generally between 0 and 180 degrees. Blade 12 may be constructed of various materials of construction including steel or alloys for example as disposable blades or more resistant materials such as diamond or sapphire which can be reused.

FIG. 2 illustrates an exemplary blade 12 extending in a horizontal plane (X-Y plane) along a longitudinal axis "X" and a lateral axis "Y" orthogonal to the longitudinal axis, the blade is laterally symmetric about the longitudinal axis. Blade 12 includes a first triangular portion 22 having first, opposed, cutting edges 22a, 22b and a first longitudinal length 22L extending from anterior tip 16 to a first position 24. First position 24 has a first width 24W parallel to the lateral axis Y. A second portion 26 has parallel second edges 26a, 26b and a second longitudinal length 26L extending from first position 24 to a second position 28. Second position 28 has a width 28W equal to first width 24W. Blade 12 has a third portion 30 having third, opposed, cutting edges 30a, 30b and a third longitudinal length 30L extending from the second position 28 to a third position 32, the third position has a third width 32W that is greater than first width 24W. It will be recognized that blade 12 may be constructed of a single, continuous piece of material, or constructed of two or more pieces of material, that may be interconnected in the form of blade 12 prior to being connected to a handle or interconnected by the connection of the pieces to the handle.

In some embodiments, such as illustrated in FIG. 2, the third opposed cutting edges 30a, 30b do not extend at a constant angle from the second position to the third position. An angle relative to the longitudinal axis includes an arc. In FIG. 2, third opposed cutting edges 30a, 30b extend from second position 28 to an intermediate point, or position, 34 at an anterior angle 36 relative to the longitudinal axis "X" and extends from intermediate point 34 to third position 32 at a posterior angle 38 relative to the longitudinal axis that is different from anterior angle 36. Blade 12 has a third intermediate width 34W. The first or anterior leg 31 of third opposed cutting edges 30a, 30b has a longitudinal length of 30L-1 and the second or posterior leg 33 of third opposed cutting edges 30a, 30b has a longitudinal length of 30L-2.

In this embodiment, blade 12 has a terminal portion 40 that extends longitudinally away from third position 32 and anterior tip 16 toward elbow 18. The opposed terminal edges 40a, 40b taper inward (toward center axis X) so that a terminal width 40W of the terminal portion narrows from third width 32W. Terminal portion 40 extends a longitudinal length 40L for example to elbow 18.

In a non-limiting example, first length 22L and the first width 24W are each about 1 mm, second longitudinal length 26L is about 2 mm, third width 32W is about 2.0 mm to 3.4 mm, and third length 30L is about 1 mm. When applicable, length 30L-1 and 30L-2 may be equal, for example, about 0.5 mm when third length 30L is about 1 mm. In a non-limiting example, intermediate width 34W is about 2.0 mm and third width 32W is about 2.4 mm where the first and second widths are each about 2 mm.

First width 24W may be in the range, for example, of about 0.8 mm to 1.4 mm. First width 24W may be less than 1 mm or greater than 1 mm. The largest width, third width 32W may be for example in the range of about 1.4 mm to 3.4 mm. In another example, the third width may be in the range of about 2.0 to 3.4 mm. In another example, the third width is in the range of about 2.0 mm to 3.2 mm.

Figure 3:
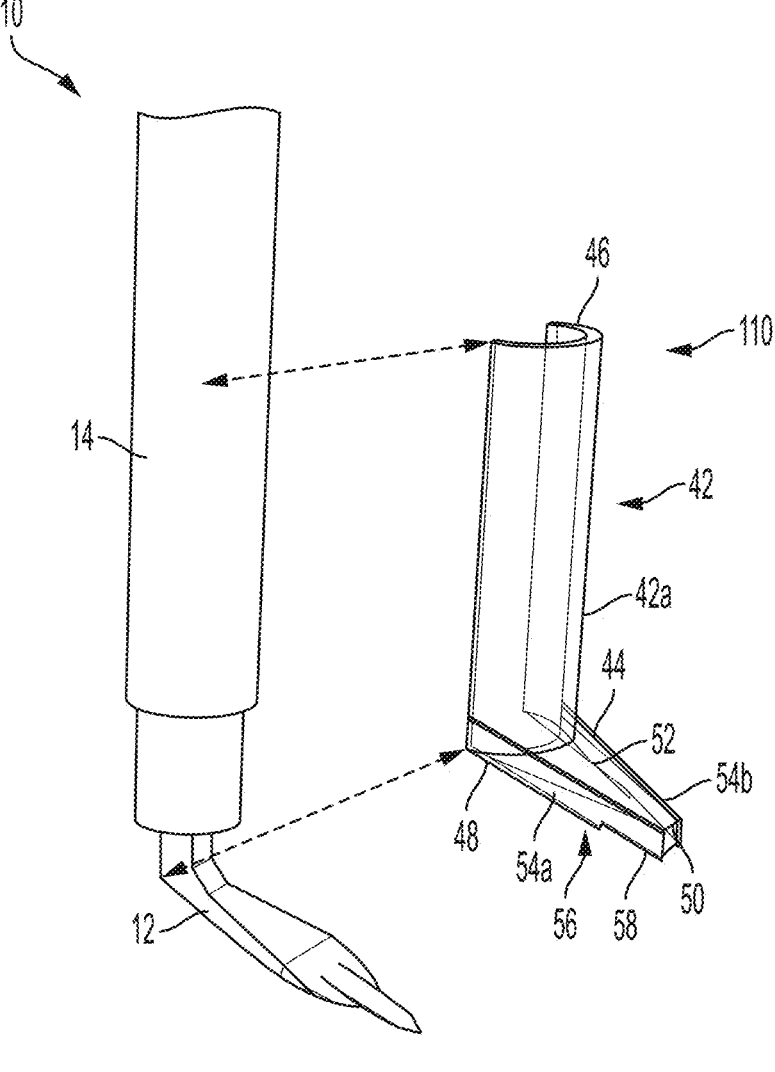
FIG. 3 illustrates an exemplary with ophthalmic instrument in a full operational position with an exemplary guard removed from attachment with the instrument according to one or more aspects of the disclosure.
Figure 4:
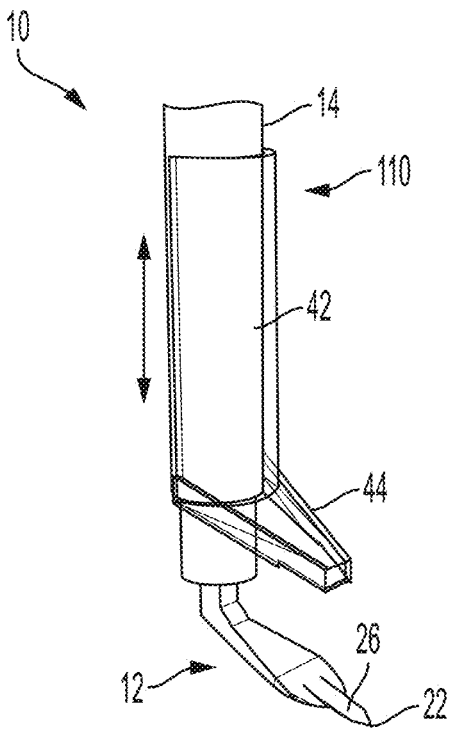
FIG. 4 illustrates an exemplary with ophthalmic instrument in a full operational position with an exemplary guard attached to the instruments handle and moved to a position exposing all cutting edges of the blade for creating an incision.
Figure 5:
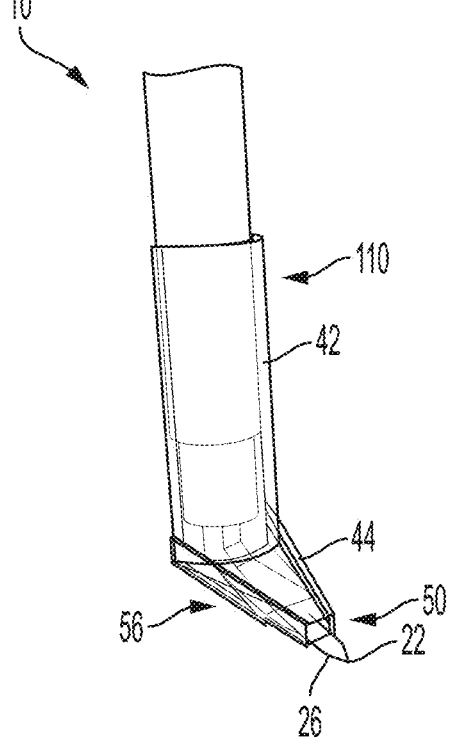
FIG. 5 illustrates an exemplary with ophthalmic instrument in a partial operational position with an exemplary guard covering aft cutting edges and exposing front cutting edges for creating an incision with the forward cutting edges.

Embodiments and methods disclosed herein utilize a new guard. FIGS. 3-5 illustrate an exemplary guard 40. Guard 40 is configured for moveable connection with an ophthalmic instrument 10. Guard 40 includes a first leg 42 and a second leg 44. First leg 42 is configured to attach to handle 14 and be moveable relative to the handle. First leg 42 may be moveable along the length of the handle or removable from the handle. The illustrated first leg 42 is a partial, semi-circular, cylinder for snapping on to handle 14. First leg 42 is an elongate cylinder or semi-cylinder extending from a top end 46 to a bottom end 48. Second leg 44 extends away from a front side 42a of first leg 42 to a front end 50. Front end 50 is open to pass triangular portion 22 and second portion 26 when guard 40 is in a partial operational position (FIG. 5). Second leg 44 has a top side 52 and opposed sides 54a, 54b formed of the material of construction and extending to front end 50. Forming an internal cavity 56 that is open at a bottom side 58 of second leg 44.

FIG. 4 illustrates guard 110 positioned on the handle 14 of instrument 10. First leg 42 is attached to handle 14 and guard 110 is axially moveable on handle 14. In the full operational position blade 12 is completely removed from second leg 44 whereby each of the cutting edges for blade 12 can be used. It should be recognized that the full operational position can be achieved by removal of guard 110 from instrument 10 as shown in FIG. 3.

FIG. 5 illustrates guard 110 in a partial operational position. In the partial operational position, the aft portion of blade 12 is positioned inside of second leg 44 with second portion 26 and first triangular portion 22 extending through front end 50 and exposed for use to create an incision in a cornea.

As previously noted, blade 12 may be formed by a single, continuous piece of material, or two or more pieces that are interconnected to provide the stepped shape and different cutting edges. FIGS. 6-9 illustrate exemplary aspects of blades 12 formed of two or more pieces of material, which are described with reference to FIGS. 1-2. Using two or more pieces with the cutting edges on different pieces may promote more efficient and effective sharpening of the cutting edges.

Figure 6:
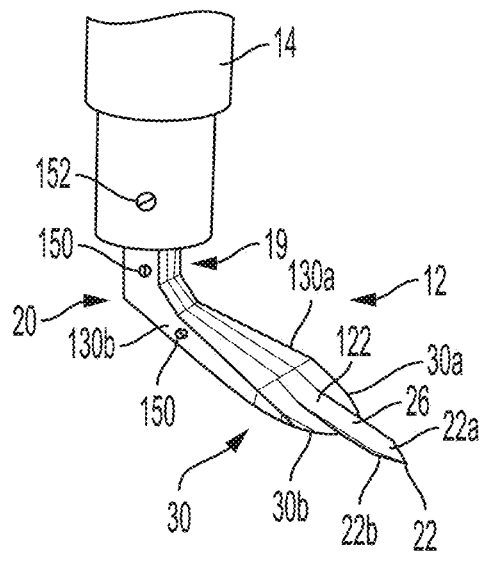
FIG. 6 illustrates an exemplary multifunction ophthalmic blade constructed of two or more separate pieces of material.

FIG. 6 illustrates a blade 12 formed of two or more pieces of material. Blade 12 includes an anterior piece 122 of material carrying first triangular portion 22, first opposed cutting edges 22a, 22b, and second portion 26. Anterior piece 122 cooperates with and is interconnected with one or more lateral pieces of material carrying third portion 30 and cutting edges 30a, 30b. For example, in FIG. 6 blade 12 includes a first lateral piece 130a having third cutting edge 30a and a second lateral piece 130b. Lateral pieces 130a, 130b, and anterior piece 122 are aligned to form the desired multiple cutting edge blade 12. Anterior piece 122 and lateral pieces 130a, 130b may each include a portion of elbow 20 and arm 19. The pieces of blade 12 may be interconnected by various fasteners including without limitation screws, pins, welds, solder, friction fit, and adhesives. For example, FIG. 6 illustrates blade fasteners 150 in the form of screws or pins that hold the pieces together as blade 12 even when blade 12 is not connected to handle 12. Blade 12 is illustrated as attached via arm 19 to handle 14 via handle fastener 152 which again is shown in the form of a screw or pin that facilitates detaching blade 12 from the handle. Handle fastener 152 may serve as the fastener that interconnects the pieces together in the blade 12 configuration.

Figure 7:
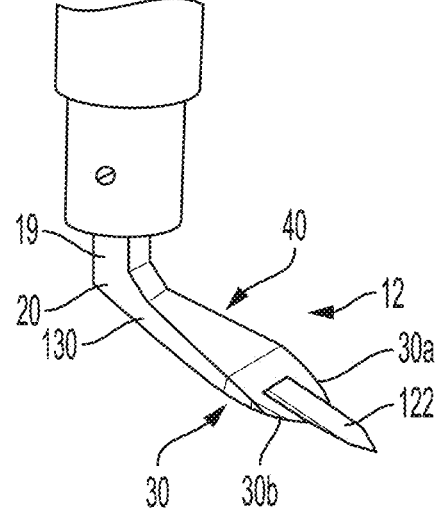
FIG. 7 illustrates an exemplary multifunction ophthalmic blade constructed of two separate pieces of material.
Figure 8:
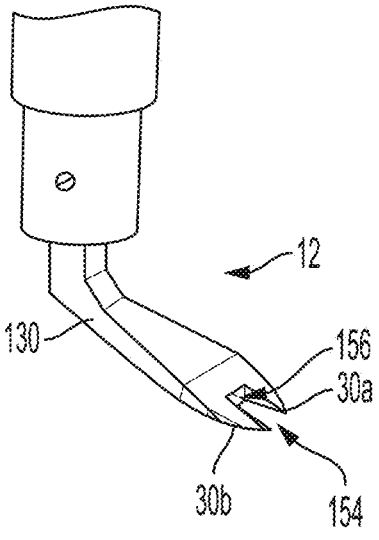
FIG. 8 illustrates an exemplary multifunction ophthalmic blade constructed of two separate pieces of material with an anterior piece removed.
Figure 9:
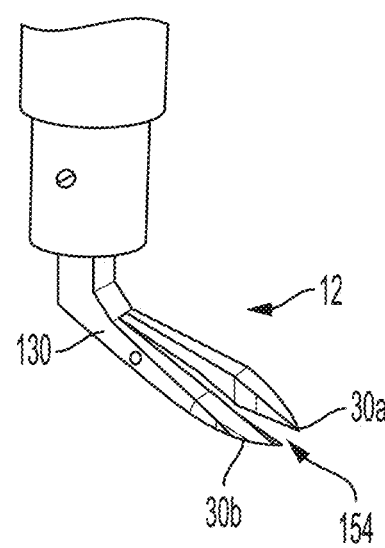
FIG. 9 illustrates another exemplary multifunction ophthalmic blade constructed of two separate pieces of material with an anterior piece removed.

FIGS. 7-9 illustrate exemplary aspects of blade 12 constructive of two separate pieces of material, anterior piece 122 including the first triangular portion and the second portion and a lateral piece 130 that includes third portion 30, third opposed cutting edges 30a, 30b, terminal portion 40, elbow 20 and arm 19.

Anterior piece 122 is removed in FIGS. 8-9 illustrating lateral piece 130 alone. In each of FIGS. 8 and 9, lateral piece 130 creates an opening 154 between third opposed cutting edges 30a, 30b in which the anterior portion is to be positioned. In FIG. 8, lateral piece 130 may form a cavity 156 between edges 30a, 30b into which a portion of the anterior piece can be inserted.

Figure 10:
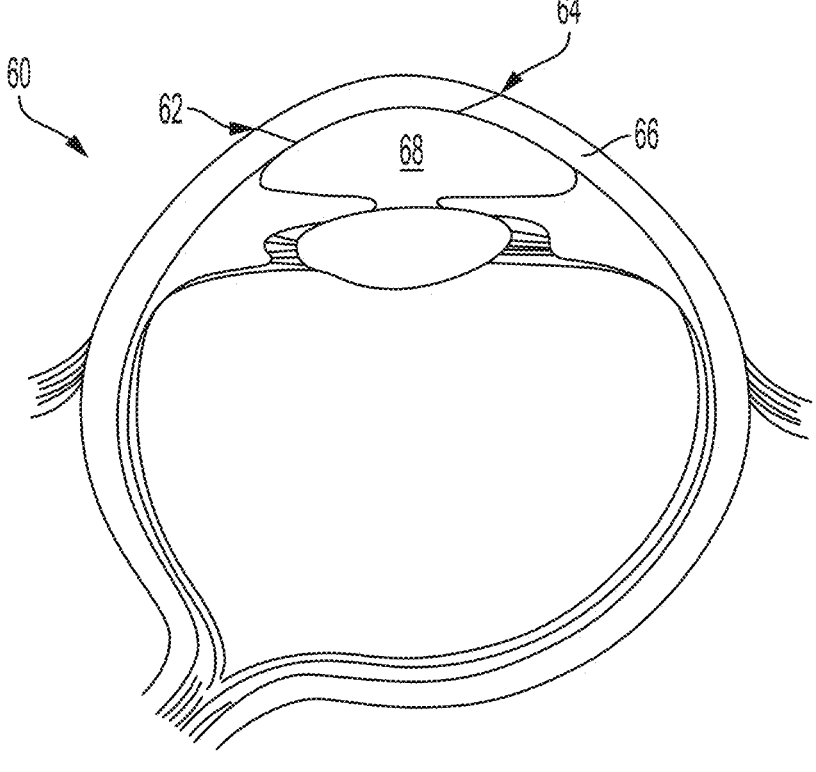
FIG. 10 is a diagrammatic sectional view of a human eye.

FIG. 10 is a diagrammatic sectional view of a human eye 60. Blade 12 can be used to create incisions 62, 64 in the cornea 66 and into the anterior chamber 68. An exemplary method is described with reference to FIGS. 1-10. Guard 110 is positioned on an ophthalmic instrument 10 in a partial operational position as shown in FIG. 5. With guard 110 in the partial operational position, instrument 10 is manipulated to create an incision 62, e.g., "side port" incision, in the cornea by passing first triangular portion 22 into cornea 66. Guard 110 prevents accidentally creating a larger incision by maintaining the third portion with cutting edges inside of the guard. To create the "main incision" 64 in the cornea, guard 110 is moved to the full operational position and first triangular section 22 and third opposed cutting edges 30a, 30b are used to create the main incision 64. Guard 110 may be removed from instrument 10 for the full operational position. In some embodiments, guard 110 may be axially moved thereby removing blade 12 from inside of second leg 44 of the guard exposing the third opposed cutting edges. Guard 110 may be rotated moving second leg 44 from directly above blade 12.

Although relative terms such as "outer," "inner," "upper," "lower," and similar terms have been used herein to describe a spatial relationship of one element to another, it is understood that these terms are intended to encompass different orientations of the various elements and components in addition to the orientation depicted in the figures. Furthermore, as used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements. The terms "substantially," "approximately," "generally," and "about" are defined as largely but not necessarily wholly what is specified (and includes what is specified; e.g., substantially 90 degrees includes 90 degrees and substantially parallel includes parallel), as understood by a person of ordinary skill in the art. The extent to which the description may vary will depend on how great a change can be instituted and still have a person of ordinary skill in the art recognized the modified feature as still having the required characteristics and capabilities of the unmodified feature.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. An ophthalmic instrument, comprising:
a blade extending in a horizontal plane along a longitudinal axis and a lateral axis orthogonal to the longitudinal axis, the blade laterally symmetric about the longitudinal axis, wherein the blade comprises:
a first triangular portion having first opposed cutting edges and a first longitudinal length extending from an anterior tip to a first position, the first position having a first width parallel to the lateral axis;
a second portion having parallel second edges and a second longitudinal length extending from the first position to a second position;
a third portion having third opposed cutting edges and a third longitudinal length extending from the second position to a third position, the third position having a third width that is greater than the first width; and
a terminal portion extending longitudinally from the third position to an elbow having an elbow angle less than 180 degrees relative to the horizontal plane;
a handle extending from the elbow; and
a guard comprising a first leg and a second leg;
the first leg having a front side extending axially from a top end to a bottom end, the first leg moveably attached to the handle with the bottom end between the top end and the blade; and
the second leg having a top side extending from the front side and the bottom end of the first leg to a front end and the second leg is open on a bottom side opposite from the top side:
wherein the guard is moveable between a partial operational position with the front end located on the second position allowing the first triangular portion and the second portion to be inserted into tissue and blocking the third portion and the third opposed cutting edges and a full operational position removing the second leg from the blade and exposing the first opposed cutting edges and the third opposed cutting edges.

2. The ophthalmic instrument of claim 1, wherein the terminal portion has a terminal width narrowing from the third width to the elbow.

3. The ophthalmic instrument of claim 1, wherein the third opposed cutting edges do not extend at a constant angle, relative to the longitudinal axis, from the second position to the third position.

4. The ophthalmic instrument of claim 1, wherein the third opposed cutting edges extend from the second position to an intermediate point at an anterior angle relative to the longitudinal axis and extend from the intermediate point to the third position at a posterior angle relative to the longitudinal axis that is different from the anterior angle.

5. The ophthalmic instrument of claim 1, wherein the first width is about 1 mm and the third width is about 1.4 to 3.4 mm.

6. The ophthalmic instrument of claim 1, wherein the first width is about 1 mm and the third width is about 1.4 to 2.4 mm.

7. The ophthalmic instrument of claim 1, wherein the first width is about 1 mm, the first longitudinal length is about 1 mm, the second longitudinal length is about 2 mm, and the third width is about 1.4 to 3.4 mm.

8. The ophthalmic instrument of claim 1, wherein:
the first width is about 1 mm;
the first longitudinal length is about 1 mm;
the second longitudinal length is about 2 mm;
the third width of about 2.0 to 3.4 mm; and
the third longitudinal length is about 1 mm.

9. The ophthalmic instrument of claim 8, wherein the terminal portion has a terminal width narrowing from the third width to the elbow.

10. The ophthalmic instrument of claim 1, wherein the first leg is axially moveable on the handle between the partial operational position and the full operational position.

11. The ophthalmic instrument of claim 1, wherein the first leg consists of a semi-circular member.

12. The ophthalmic instrument of claim 1, wherein the second leg comprises opposing sides extending downward from the top side and terminating at the front end.

13. The ophthalmic instrument of claim 12, wherein the first leg is axially moveable on the handle between the partial operational position and the full operational position.

14. The ophthalmic instrument of claim 12, wherein first leg consists of a semi-circular member.

15. An ophthalmic instrument, comprising:
a handle; and
a blade extending in a horizontal plane along a longitudinal axis and a lateral axis orthogonal to the longitudinal axis, the blade laterally symmetric about the longitudinal axis, wherein the blade comprises:
a first triangular portion having first opposed cutting edges and a first longitudinal length extending from an anterior tip to a first position, the first position having a first width along the lateral axis of about 1 mm;
a second portion having parallel second edges and a second longitudinal length extending from the first position to a second position, the second longitudinal length about 2 mm or greater;
a third portion having third opposed cutting edges and a third longitudinal length extending from the second position to a third position, the third position having a third width of about 2.0 to 3.4 mm; and
a terminal portion extending longitudinally from the third position to an elbow extending to the handle at an elbow angle less than 180 degrees to the horizontal plane, and the terminal portion having a terminal width narrowing from the third position; and
a guard comprising a first leg and a second leg;
the first leg having a front side extending axially from a top end to a bottom end, the first leg moveably attached to the handle; and
the second leg having a top side extending from the front side and the bottom end of the first leg to a front end and the second leg open on a bottom side opposite from the top side:
wherein the guard is moveable between a partial operational position with the front end located on the second position allowing the first triangular portion and the second portion to be inserted into tissue and blocking the third portion and the third opposed cutting edges and a full operational position removing the second leg from the blade exposing the first opposed cutting edges and the third opposed cutting edges.

16. The ophthalmic instrument of claim 15, wherein the third opposed cutting edges extend from the second position to an intermediate point at an anterior angle relative to the longitudinal axis and extend from the intermediate point to the third position at a posterior angle relative to the longitudinal axis that is different from the anterior angle.

17. The ophthalmic instrument of claim 15, wherein the first leg is axially moveable on the handle between the partial operational position and the full operational position.

18. The ophthalmic instrument of claim 15, wherein the first leg consists of a semi-circular member.

19. The ophthalmic instrument of claim 15, wherein the second leg comprises opposing sides extending downward from the top side and terminating at the front end.

20. The ophthalmic instrument of claim 19, wherein the first leg is axially moveable on the handle between the partial operational position and the full operational position.

21. The ophthalmic instrument of claim 19, wherein the first leg consists of a semi-circular member.

22. An ophthalmic instrument, comprising:

a blade extending in a horizontal plane along a longitudinal axis and a lateral axis orthogonal to the longitudinal axis, the blade laterally symmetric about the longitudinal axis, wherein the blade comprises:

a first triangular portion having first opposed cutting edges and a first longitudinal length extending from an anterior tip to a first position, the first position having a first width parallel to the lateral axis;

a second portion having parallel second edges and a second longitudinal length extending from the first position to a second position; and a third portion having third opposed cutting edges and a third longitudinal length extending from the second position to a third position, the third position having a third width that is greater than the first width;

a handle; and a guard comprising a first leg and a second leg;

the first leg having a front side extending axially from a top end to a bottom end, the first leg moveably attached to the handle with the bottom end between the top end and the blade; and the second leg extending from the front side proximate the bottom end of the first leg to a front end, the second leg comprising a top side and a pair of opposing sides defining a cavity with an open bottom side opposite from the top side:

wherein the guard is axially moveable on the handle between a partial operational position with the front end located on the second position allowing the first triangular portion and the second portion to be inserted into tissue and blocking the third portion and the third opposed cutting edges and a full operational position removing the second leg from the blade and exposing the first opposed cutting edges and the third opposed cutting edges.

* * * * *